United States Patent
Martinez Martinez

(10) Patent No.: US 6,852,286 B2
(45) Date of Patent: Feb. 8, 2005

(54) DEVICE FOR EXTRACTING AND TAKING SAMPLES FROM AN AQUEOUS SOLUTION IN A SUBSTRATE

(76) Inventor: Estanislao Martinez Martinez, Avda. Nuestra Señora Aguas Santas, 55, 4318 Villaverde del Rio (Sevilla) (ES)

( * ) Notice: Subject to any disclaimer, the term of this patent is extended or adjusted under 35 U.S.C. 154(b) by 225 days.

(21) Appl. No.: 09/813,949

(22) Filed: Mar. 22, 2001

(65) Prior Publication Data

US 2001/0051111 A1 Dec. 13, 2001

(30) Foreign Application Priority Data

Jun. 9, 2000 (ES) ...................................... 200001559 U

(51) Int. Cl.[7] .............................................. G01N 31/00
(52) U.S. Cl. ...................... 422/99; 422/102; 422/100; 422/103; 436/31; 436/28; 436/30
(58) Field of Search ................. 422/913, 916, 422/918, 99, 102; 435/788.1, 304.1; D24/224; 436/31, 28, 30; 73/152.01–152.62, 73

(56) References Cited

U.S. PATENT DOCUMENTS

| | | | | |
|---|---|---|---|---|
| 2,878,671 A | * | 3/1959 | Prosser et al. ................. | 73/73 |
| 3,028,313 A | * | 4/1962 | Oberdorfer, Jr. et al. ....... | 435/9 |
| 3,043,133 A | * | 7/1962 | Richards ........................ | 73/73 |
| 3,045,477 A | * | 7/1962 | Matson ........................... | 73/73 |
| 3,049,914 A | * | 8/1962 | Richards ........................ | 73/73 |
| 3,091,115 A | * | 5/1963 | Roberts .......................... | 73/73 |
| 3,318,140 A | * | 5/1967 | Oberdorfer, Jr. et al. ....... | 73/73 |
| 3,705,018 A | * | 12/1972 | Taylor .......................... | 422/100 |
| 3,858,441 A | * | 1/1975 | Comeau ........................ | 73/784 |
| 3,871,211 A | * | 3/1975 | Tal ................................ | 73/73 |
| 3,898,872 A | * | 8/1975 | Skaling et al. ................. | 73/73 |
| 3,958,944 A | * | 5/1976 | Wong ............................ | 422/72 |
| 4,009,078 A | * | 2/1977 | Wilkins et al. ................ | 205/778 |
| 4,068,525 A | * | 1/1978 | Skaling ......................... | 73/73 |
| 4,137,931 A | * | 2/1979 | Hasenbeck .................. | 137/78.3 |
| 4,200,493 A | * | 4/1980 | Wilkins et al. ........ | 204/403.01 |
| 4,383,543 A | * | 5/1983 | Rawlins ...................... | 137/78.3 |
| 4,438,654 A | * | 3/1984 | Torstensson ............. | 73/864.52 |
| 4,453,401 A | * | 6/1984 | Sidey ............................. | 73/73 |
| 4,520,657 A | * | 6/1985 | Marthaler ...................... | 73/73 |
| 4,531,087 A | * | 7/1985 | Larson ....................... | 324/696 |
| 4,692,287 A | * | 9/1987 | Timmons ..................... | 264/41 |
| 4,759,227 A | * | 7/1988 | Timmons ................. | 73/863.23 |
| 4,807,707 A | * | 2/1989 | Handley et al. .............. | 175/20 |
| 4,922,945 A | * | 5/1990 | Browne .................... | 137/78.3 |
| 4,953,637 A | * | 9/1990 | Starr et al. .................... | 175/20 |
| 5,000,051 A | * | 3/1991 | Bredemeier ............. | 73/863.23 |
| 5,010,776 A | * | 4/1991 | Lucero et al. ........... | 73/863.23 |
| 5,035,149 A | * | 7/1991 | Wierenga ................ | 73/863.23 |
| 5,080,868 A | * | 1/1992 | Elgas .......................... | 422/99 |
| 5,147,612 A | * | 9/1992 | Raal ............................ | 422/99 |
| 5,161,407 A | * | 11/1992 | Ankeny et al. ................ | 73/38 |
| 5,179,347 A | * | 1/1993 | Hawkins ..................... | 324/696 |
| 5,400,858 A | * | 3/1995 | Blanchard et al. .......... | 166/370 |
| 5,432,098 A | * | 7/1995 | Wilks ........................ | 436/178 |
| 5,445,795 A | * | 8/1995 | Lancaster et al. ............. | 422/86 |

(List continued on next page.)

FOREIGN PATENT DOCUMENTS

| | | | | |
|---|---|---|---|---|
| FR | 2788598 A1 | * | 7/2000 | ............ G01N/1/10 |
| GB | 2137760 A | * | 10/1984 | ......... G01N/33/24 |
| JP | 01172731 A | * | 7/1989 | ............ G01N/1/14 |

Primary Examiner—Jill Warden
Assistant Examiner—Sam P. Siefke
(74) Attorney, Agent, or Firm—Crowell & Moring LLP

(57) ABSTRACT

A device is provided for extraction of samples of an aqueous solution in a substratum. A probe made up of a pyrometric capsule of porous porcelain has one end of lesser diameter to which is attached a tube of inert material. The tube is sealed hermetically by a rubber cap with two drilled holes. An adapted pipe is fitted into one of the drilled holes for connection to a vacuum pump, and a suction capillary is placed in the other drilled hole.

2 Claims, 1 Drawing Sheet

U.S. PATENT DOCUMENTS

| | | | | |
|---|---|---|---|---|
| 5,481,927 A | * | 1/1996 | Hubbell et al. | 73/863.71 |
| 5,525,298 A | * | 6/1996 | Anami | 422/63 |
| 5,578,455 A | * | 11/1996 | Tosa et al. | 435/7.32 |
| 5,644,947 A | * | 7/1997 | Hubbell et al. | 73/73 |
| 5,758,538 A | * | 6/1998 | Hubbell et al. | 73/73 |
| 5,783,155 A | * | 7/1998 | Greenler et al. | 422/102 |
| 5,871,699 A | * | 2/1999 | Ruggeri | 422/100 |
| 5,891,740 A | * | 4/1999 | Di Cesare et al. | 436/518 |
| 5,900,545 A | * | 5/1999 | Sacks et al. | 73/152.52 |
| 5,902,939 A | * | 5/1999 | Ballard et al. | 73/863.12 |
| 5,915,476 A | * | 6/1999 | Hubbell et al. | 166/113 |
| 5,922,950 A | * | 7/1999 | Pemberton et al. | 73/152.28 |
| 5,941,121 A | * | 8/1999 | Faybishenko | 73/73 |
| 6,045,753 A | * | 4/2000 | Loewy et al. | 422/57 |
| 6,179,787 B1 | * | 1/2001 | Kelly et al. | 600/573 |
| 6,270,727 B1 | * | 8/2001 | Mitchell et al. | 422/102 |
| 6,289,725 B1 | * | 9/2001 | Hubbell et al. | 73/73 |

* cited by examiner

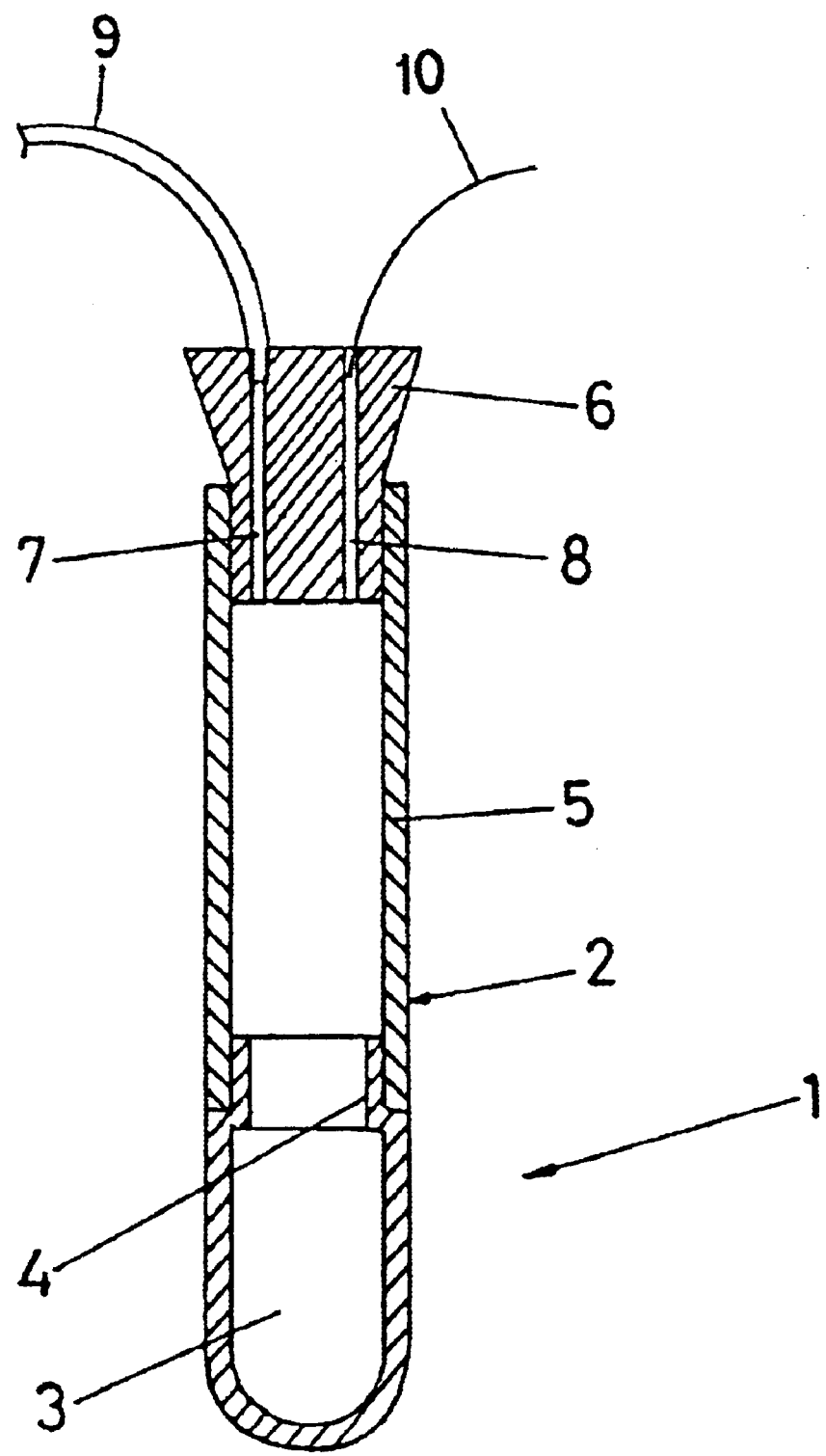

DEVICE FOR EXTRACTING AND TAKING SAMPLES FROM AN AQUEOUS SOLUTION IN A SUBSTRATE

BACKGROUND OF THE INVENTION

This application claims priority of Spanish Application Serial No. 200001559, filed on Jun. 9, 2000, the disclosure of which is expressly incorporated by reference herein.

Known procedures and devices carry out the collection of a soil sample which is taken to the laboratory. This has the inconvenience that the aqueous solution found in the edaphic profile or substratum is not used directly, and thus the degree of distortion of the analysis depends mainly on the qualitative composition of the water used.

SUMMARY OF THE INVENTION

An object of the present invention is a device used to extract and take samples from an aqueous solution in a substrate.

The device of the present invention is applied to carry out the extraction and sampling of an aqueous substrate solution in, for example, soils with different edaphic profiles or substratum, called soil solution; land drainage; artificial inorganic substrata, saturated or unsaturated; and artificial organic substrata, saturated or unsaturated.

The device is usable, in particular, for agricultural, environmental and industrial applications.

Among others, the following specific agricultural applications can be mentioned: studies of the composition of different chemical forms, evolution and degradation of organic compounds (chelates) and inorganic compounds in their different chemical forms. Also, the present invention is usable to discover the evolution and availability of fertilizing nutrients in general, over the whole soil profile.

In the environmental area, the device is used to control polluting effluents such as nitrates, nitrites, fitosanitary compounds in general, chemical evolution of inorganic compounds, organic compounds (chelates, remains of pesticides), and the control of aquifers.

In the industrial area, the device is used to control ponds for decanting solids and/or liquids, and residue control.

This capsule has a step shape on the end perimeter to which is attached a tube of total inert material such as P.V.C., polyethylene, etc. and of external diameter which is preferably the same as the external diameter of the capsule.

At the free end of the tube, a rubber pipe with hermetic closure is attached. An adapter tube for a vacuum pump and a suction gland that is introduced lengthways into the probe are provided in the closure.

BRIEF DESCRIPTION OF THE DRAWINGS

Other objects, advantages and novel features of the present invention will become readily apparent from the following detailed description of the invention when considered in conjunction with the accompanying drawings.

The sole FIGURE is a sectional view of the device of the invention in the form of a probe for extracting and taking samples of aqueous substrate solutions.

DETAILED DESCRIPTION OF THE DRAWINGS

This device designated generally by numeral 1 is constituted by a probe generally designated by numeral 2 formed by a capsule 3 of porous porcelain having a decreased section 4 in the end area, to which is attached the end of a pipe 5 of known inert material, such as P.V.C., polyethylene, etc.

A rubber cap 6 is attached on the free end of the tube 5 to obtain a hermetic seal.

Two holes 7,8 are drilled into cap 6 into one of which holes is attached the end of an adapter tube 9 to a vacuum pump (not shown) and in the other hole is attached a capillary suction tube 10 which is the one placed inside the probe.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Device for extraction of samples of an aqueous solution in a substratum, comprising a probe including a pipe of inert material, a capsule of porous porcelain with an end of lesser diameter than another end to which is attachable the pipe of inert material, and a rubber cap with drilled holes hermetically sealing the pipe, an adapter tube being fitted into one of the holes and being connectable to a vacuum pump, and a capillary suction tube that is placeable inside the probe being fitted into another of the holes.

2. Device for extraction and sampling from an aqueous solution of substrate, comprising a probe consisting of a capsule of porous porcelain fitted with an end zone of smaller diameter to which a tube of inert material is attached, the end of which is sealed hermetically with a rubber cap adaptable for connection to a vacuum pump and through which a suction capillary is introducible into the probe interior.

* * * * *